United States Patent
Hamasaki et al.

(10) Patent No.: US 11,921,021 B2
(45) Date of Patent: Mar. 5, 2024

(54) GAS CONCENTRATION DEVICE, GAS DETECTION SYSTEM, GAS CONCENTRATION METHOD, AND GAS DETECTION METHOD

(71) Applicant: Kabushiki Kaisha Toshiba, Tokyo (JP)

(72) Inventors: Hiroshi Hamasaki, Hiratsuka Kanagawa (JP); Yoshiaki Sugizaki, Fujisawa Kanagawa (JP)

(73) Assignee: Kabushiki Kaisha Toshiba, Tokyo (JP)

(*) Notice: Subject to any disclaimer, the term of this patent is extended or adjusted under 35 U.S.C. 154(b) by 269 days.

(21) Appl. No.: 17/462,997

(22) Filed: Aug. 31, 2021

(65) Prior Publication Data

US 2022/0307952 A1    Sep. 29, 2022

(30) Foreign Application Priority Data

Mar. 23, 2021 (JP) .................. 2021-048503

(51) Int. Cl.

| | | |
|---|---|---|
| G01N 33/68 | (2006.01) | |
| A01N 1/02 | (2006.01) | |
| B01L 3/00 | (2006.01) | |
| C07C 309/65 | (2006.01) | |
| C07C 309/73 | (2006.01) | |
| G01N 1/40 | (2006.01) | |
| G01N 21/33 | (2006.01) | |
| G01N 21/64 | (2006.01) | |
| G01N 27/414 | (2006.01) | |
| G01N 33/52 | (2006.01) | |

(Continued)

(52) U.S. Cl.
CPC ....... *G01N 1/4077* (2013.01); *G01N 27/4141* (2013.01)

(58) Field of Classification Search
CPC ............. G01N 1/4077; G01N 27/4141; G01N 33/0016
See application file for complete search history.

(56) References Cited

U.S. PATENT DOCUMENTS 5,465,578 A * 11/1995 Barben .................. F25B 21/02
                                                        136/203
2019/0086376 A1 * 3/2019 Ehrling .............. G01N 33/0009
(Continued)

FOREIGN PATENT DOCUMENTS

JP          2005-3387 A       1/2005
JP    WO 2003036696 A1 *      2/2005
(Continued)

*Primary Examiner* — Jennifer Wecker
*Assistant Examiner* — Oyeleye Alexander Alabi
(74) *Attorney, Agent, or Firm* — Finnegan, Henderson, Farabow, Garrett & Dunner, LLP (57) ABSTRACT

A gas concentration device includes a first container, a second container, a pressure control device, and a path. The first container includes a first space surrounded by a first partition wall and stores a specimen, and a pressure inside the first space is reduced. The second container is airtightly connected to the first container by a first path and has a second space surrounded by a second partition wall and stores a gas flowing in from the first space. The pressure control device reduces a volume of the second space. A gas inside the second space is discharged through a second path.

22 Claims, 8 Drawing Sheets

(51) Int. Cl.
*G01N 33/532* (2006.01)
*G01N 33/543* (2006.01)
*G01N 33/569* (2006.01)
*G01N 33/72* (2006.01)

(56) References Cited

U.S. PATENT DOCUMENTS

2019/0293596 A1\* 9/2019 Nakamura ............. G01N 27/22
2022/0187265 A1\* 6/2022 Tobjork ............. G01N 33/0016

FOREIGN PATENT DOCUMENTS

JP 2012-181123 A 9/2012
JP 2012181123 A \* 9/2012

\* cited by examiner

GAS CONCENTRATION DEVICE, GAS DETECTION SYSTEM, GAS CONCENTRATION METHOD, AND GAS DETECTION METHOD

CROSS-REFERENCE TO RELATED APPLICATIONS

This application is based upon and claims the benefit of priority from Japanese Patent Application No. 2021-048503 filed on Mar. 23, 2021, and the entire contents of which are incorporated herein by reference.

FIELD

Embodiments described herein relate generally to a gas concentration device, a gas detection system, a gas concentration method, and a gas detection method.

BACKGROUND

A chemical sensor that detects a substance in air can be used for gas detection and odor detection by detecting a component released from a specimen into the air.

High sensitivity is required for the gas detection and odor detection.

DETAILED DESCRIPTION

Hereinafter, embodiments of the present invention will be described with reference to the drawings.

Portions denoted by the same reference numerals indicate the same portions. Note that the drawings are schematic or conceptual, and a relationship between a thickness and a width of each portion, a ratio coefficient of sizes between the portions, and the like are not necessarily the same as actual ones.

In addition, even in the case of representing the same portion, dimensions and ratio coefficients may be represented differently from each other depending on the drawings.

First Embodiment

A gas detection system 1000 according to a first embodiment will be described with reference to FIG. 1.

Figure 1:
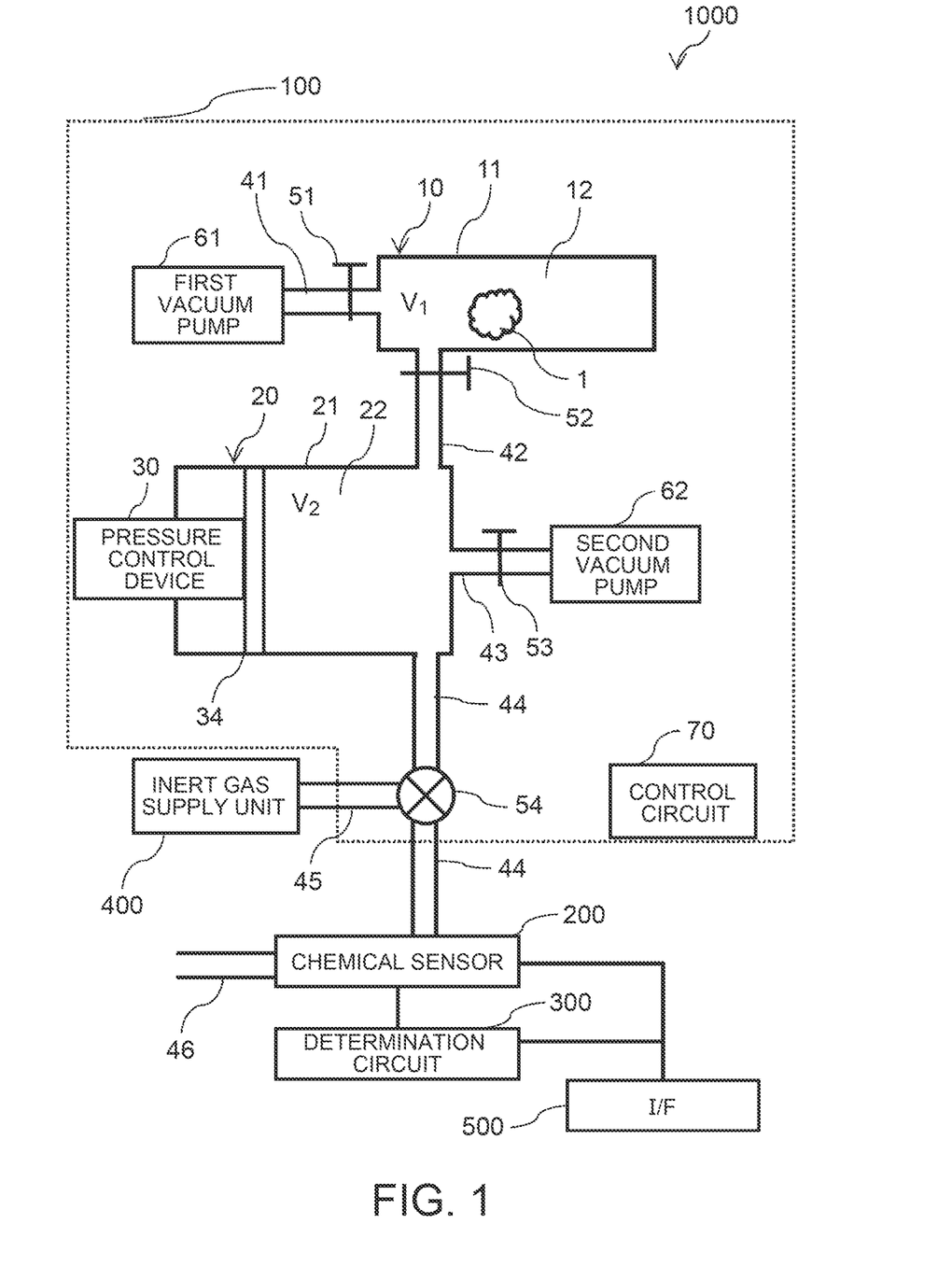
FIG. 1 is a schematic diagram illustrating a configuration of a gas detection system according to a first embodiment.

FIG. 1 is a schematic diagram illustrating a configuration of the gas detection system 1000 of the first embodiment.

The gas detection system 1000 is a system that detects a substance (odor component) of a detection target released from a specimen 1 to the atmosphere. The gas detection system 1000 includes a gas concentration device 100, a chemical sensor 200, a determination circuit 300, an inert gas supply unit 400, and an interface 500. In the present specification, the odor component refers to a substance in a gas phase that can be detected by a chemical sensor, and is not necessarily a substance that reacts with an olfactory receptor (odor receptor) of a living body.

The gas concentration device 100 includes a first container 10, a second container 20, a pressure control device 30, first to sixth airtight paths 41, 42, 43, 44, 45, and 46, first to fourth shutters 51, 52, 53, and 54, a first vacuum pump 61 as a first decompression device, a second vacuum pump 62 as a second decompression device, and a control device 70.

The first container 10 is an airtight container that has an intake port (not illustrated) for taking in and out the specimen 1 and stores the specimen 1 taken in from the intake port. The first container 10 has a first partition wall 11 and a first space 12 surrounded by the first partition wall 11. The first partition wall 11 has a structure in which a gas cannot freely move between the inside and the outside of the first space 12. The first space 12 is a space for storing the specimen 1. Even if a pressure difference is generated between the inside and the outside of the first space 12, the first partition wall 11 is not greatly deformed, and a volume of the first space 12 is maintained. A volume V1 of the first space 12 is a volume that can be accommodated in the first space 12, in other words, a volume of a gas stored in the first space 12.

The first vacuum pump 61 is connected to the first container 10 via the first airtight path 41. The first shutter 51 is provided in the first airtight path 41. Here, the airtight path refers to a structure capable of causing a gas to flow in the path while maintaining airtightness with the outside. As the airtight path, a pipe made of resin or metal can be used. The first shutter 51 can be switched between an open state in which a gas can flow in the first airtight path 41 and a closed state in which a gas cannot flow in the first airtight path 41. Therefore, the first shutter 51 can be switched between the open state in which a gas can flow between the first vacuum pump and the first container and the closed state in which a gas cannot flow between the first vacuum pump 61 and the first container 10. When the first vacuum pump 61 operates with the first shutter 51 in the open state, the gas stored in the first space 12 of the first container 10 is discharged to the atmosphere via the first airtight path 41 and the first vacuum pump 61, and a pressure inside the first space 12 is reduced. Switching of a circulation state of the first airtight path 41 can also be realized by switching on and off of the first vacuum pump 61. When the switching of the circulation state of the first airtight path 41 is realized by switching on and off of the first vacuum pump 61, the first shutter 51 can be omitted.

The second container 20 is an airtight container that stores and compresses the gas containing the substance of the detection target fed from the first space 12. The second container 20 has a second partition wall 21 and a second space 22 surrounded by the second partition wall 21. The second partition wall 21 has a structure in which a gas cannot freely move inside and outside the second space 22. The second space 22 is a space for storing the gas fed from the first space 12. The second container 20 is connected to the first container 10 via the second airtight path 42. The second shutter 52 is provided in the second airtight path 42 between the first container 10 and the second container 20. The second shutter 52 can be switched between an open state in which a gas can flow in the second airtight path 42 and a closed state in which a gas cannot flow in the second airtight path 42. Therefore, the second shutter 52 can be switched between an open state in which a gas can flow between the first container and the second container and a closed state in which a gas cannot flow between the first container 10 and the second container 20.

The second vacuum pump 62 is connected to the second container 20 via the third airtight path 43. The third shutter 53 is provided in the third airtight path 43. The third shutter 53 can switch the third airtight path 43 between the open state in which a gas can flow and the closed state in which a gas cannot flow. Therefore, the third shutter 53 can be switched between the open state in which a gas can flow between the second container and the second vacuum pump and the closed state in which a gas cannot flow between the second container 20 and the second vacuum pump 63. When the second vacuum pump 62 operates with the third shutter 53 in the open state, the gas stored in the second space 22 is discharged through the third airtight path 43, and a pressure inside the second space 22 is reduced. Switching of a circulation state of the third airtight path 43 can also be realized by switching on and off of the second vacuum pump 62. When the switching of the circulation state of the third airtight path 43 is realized by switching on and off of the second vacuum pump 62, the third shutter 53 can be omitted.

The second container 20 is connected to the chemical sensor 200 via the fourth airtight path 44. The fourth shutter 54 is provided in the fourth airtight path 44. The fourth shutter 54 is, for example, a three-way valve. One end of the three-way valve is connected to the inert gas supply unit 400 via the fifth airtight path 45. The fourth shutter 54 can be switched to at least three states of a first open state in which a gas can flow between the second space 22 and the chemical sensor 200, a second open state in which a gas can flow between the inert gas supply unit 400 and the chemical sensor 200, and a closed state in which a gas cannot flow between the second space 22, the chemical sensor 200, and the inert gas supply unit 400. The fourth shutter 54 can be switched between the first open state in which a gas can flow between the second container 20 and the chemical sensor 200 and the closed state (or a second open state) in which a gas cannot flow between the second container 20 and the chemical sensor 200. The fourth shutter 54 can be switched between the second open state in which a gas can flow between the inert gas supply unit 400 and the chemical sensor 200 and the closed state (or a first open state) in which a gas cannot flow between the inert gas supply unit 400 and the chemical sensor 200.

The pressure control device 30 is a device that increases or decreases a volume of the second space 22. A volume V2 of the second space 22 is a volume that can be accommodated in the second space 22, in other words, a volume of the gas stored inside the second space 22. The volume V2 takes a value from a maximum value V2L to a minimum value V2S. Preferably, the maximum value V2L of the volume V2 is larger than the volume V1.

The pressure control device 30 can control a gas pressure stored in the second space 22. The pressure control device 30 can take a gas in and out to the second space 22 from the airtight path in the open state by increasing or decreasing the volume of the second space 22 with the second shutter 52 in the open state. For example, when the second shutter 52 is in the closed state, the third shutter 53 is in the closed state, and the fourth shutter is in the first open state, the pressure control device 30 slowly reduces the volume of the second space 22, and thus, the gas in the second space 22 can be fed to the chemical sensor 200. The pressure control device 30 can expand or contract the gas inside the second space 22 by increasing or reducing the volume of the second space 22 in a state where all of the second shutter 52, the third shutter 53, and the fourth shutter 54 are in the closed states. When the gas inside the second space 22 expands, the gas pressure inside the second space decreases. When the gas inside the second space 22 contracts, the gas pressure increases.

A structure of the pressure control device 30 is not particularly limited as long as it can change the volume of the second space 22. As an example of the pressure control device 30, a piston-type compression mechanism is illustrated in FIG. 1. In the piston type compression mechanism, a piston 34 which is a movable partition wall in close contact with the inside of the cylinder type second partition wall 21 is provided. The volume of the second space 22 can be increased or reduced by moving the piston 34 in a lateral direction on the paper surface of FIG. 1 by power of a motor or the like inside the pressure control device 30.

A control circuit 70 is a circuit that controls each unit of the gas concentration device 100. The control device 70 is connected to the first to fourth shutters 51 to 54 and the pressure control device 30, and outputs a control signal or control signals. FIG. 1 illustrates an example in which the control device 70, the first to fourth shutters 51 to 54, and the pressure control device 30 are connected to each other in a wireless manner (not illustrated), but may be connected to each other in a wire manner. The control circuit 70 controls opening/closing timings of the first to fourth shutters 51 to 54 and an operation of the pressure control device 30 according to the output of the control signal, thereby causing the gas concentration device 100 to perform a gas concentration operation. The control circuit 70 is connected to the I/F 500. When an instruction to start the gas concentration operation is given from the I/F 500, the control circuit 70 controls each unit of the gas concentration device 100, and the gas concentration device 100 performs the gas concentration operation. The control circuit 70 may be connected not only to the operation of the gas concentration device 100 but also to the chemical sensor 200, the determination circuit 300, and the inert gas supply unit 400 to control the operation of the entire gas detection system 1000. The chemical sensor 200 may include a mechanism for taking a gas into a liquid to detect an odor component of the liquid.

The chemical sensor 200 is a device that detects a substance of the detection target contained in the gas fed from the second container 20 via the fourth airtight path 44 and outputs an electric signal represented by a voltage value, a current value, or the like to the determination circuit 300 in FIG. 1. The chemical sensor 200 may be configured to continuously detect the gas fed via the fourth airtight path 44, or may be configured to accumulate the fed gas in a collection container and feed the gas to a detection section until the fed gas reaches an amount sufficient for detection.

Figure 2:
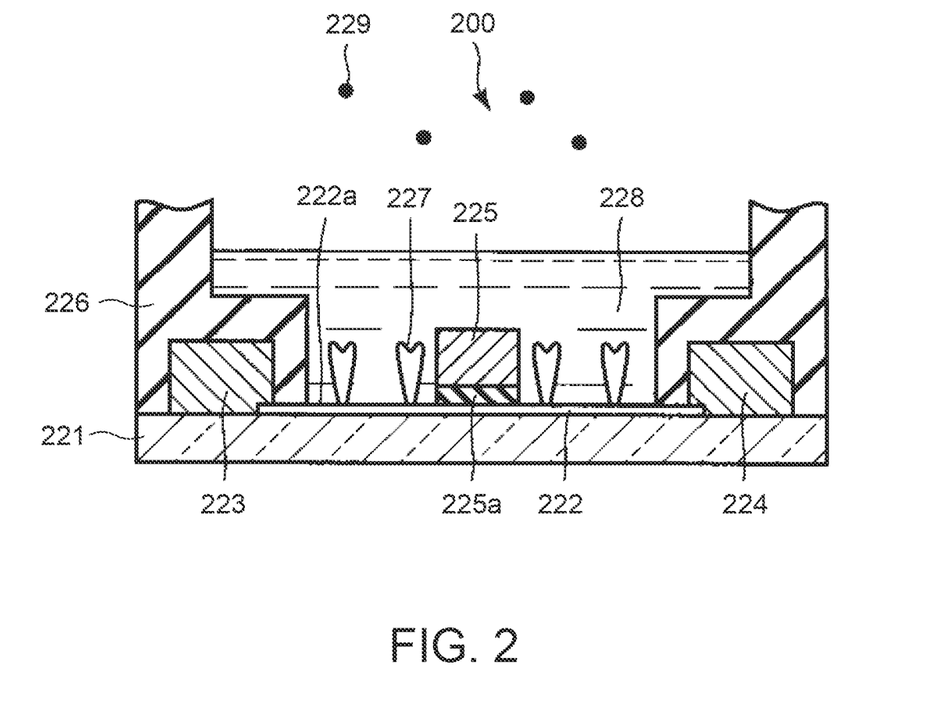
FIG. 2 is a configuration diagram illustrating an example of a chemical sensor.

As an example of the chemical sensor 200, a graphene FET device illustrated in FIG. 2 will be described. FIG. 2 is a configuration diagram illustrating an example of the chemical sensor. The graphene FET device is a field effect transistor using a sensitive membrane 222 formed of graphene on a substrate 221 as a channel. A source electrode 223 is electrically connected to one end of the sensitive membrane 222. A drain electrode 224 is provided at the other end of the sensitive membrane 222. On a sensitive membrane surface 222a located between the source electrode 223 and the drain electrode 224, a gate electrode 225 is provided via a gate insulating film 225a. A receptor 227 that binds to a substance 229 of the detection target is provided on the sensitive membrane 222, and a liquid membrane 228 is provided so as to cover the sensitive membrane 222. When a gas containing the substance 229 of the detection target is blown onto the liquid membrane 228, the substance 229 of the detection target is taken into the liquid membrane 228 and binds to the receptor 227. The graphene FET device can determine presence or absence of the substance 229 of the detection target from a drain current characteristic that changes due to the binding with the receptor 227. Since conductivity of the graphene FET device is changed depending on stress applied to the sensitive membrane 222, the graphene FET device has characteristics of low detection accuracy for a high-pressure gas and high detection accuracy for a gas close to normal pressure.

A type and a detection method of the chemical sensor 200 are not limited to the graphene FET device, and any inspection device and inspection method such as a gas chromatography device (GC), a gas chromatography mass spectrometer (GCMS), or a nuclear magnetic resonance analyzer (NMR) can be used.

The determination circuit 300 illustrated in FIG. 1 is connected to the output of the chemical sensor 200. The determination circuit 300 analyzes the output signal of the chemical sensor 200 and determines whether a specific substance contained in the gas inspected by the chemical sensor 200 is a specified amount or more. The determination circuit 300 may specify a characteristic or a type of the substance of the detection target contained in the gas inspected by the chemical sensor 200. The determination method of the determination circuit 300 is not particularly limited, and can be appropriately selected according to the type and characteristics of the chemical sensor 200. For example, the determination circuit 300 may determine whether a signal strength is equal to or more than a specified value, or may compare the signal with a reference parameter held in the determination circuit 300 to determine approximation or similarity and identify the type of the substance. The determination circuit 300 outputs a determination result to the I/F 500.

The inert gas supply unit 400 feeds nitrogen gas to the detection section of the chemical sensor 200 when the fourth shutter is in the second open state. By feeding the nitrogen gas into the chemical sensor 200 after completion of an inspection operation and discharging remaining specimen components, it is possible to prevent deterioration of detection accuracy (signal noise ratio) due to reaction of the remaining specimen components at the time of inspection of the next cycle. In the inert gas supply unit 400, as the gas to be supplied, the nitrogen gas may be replaced with any type of gas that does not contaminate the chemical sensor 200.

Figure 3:
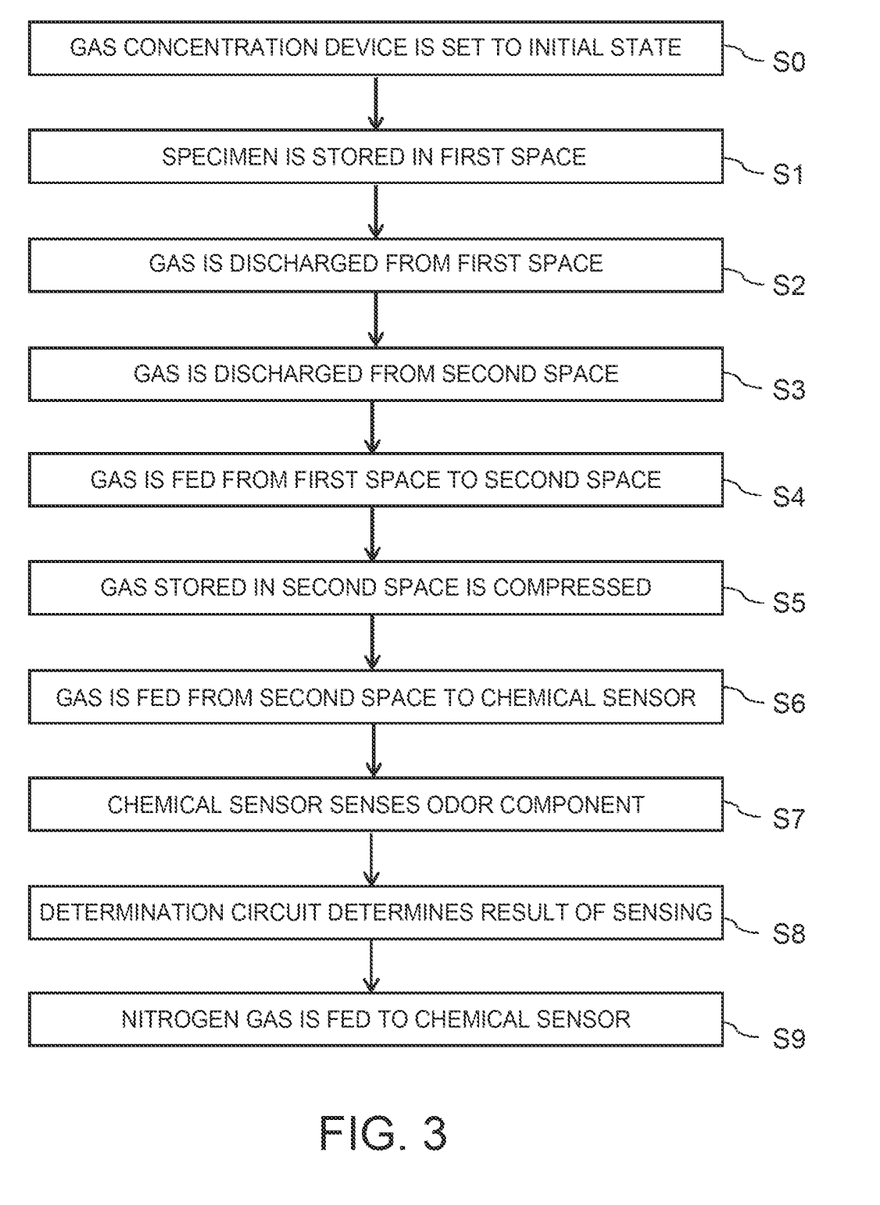
FIG. 3 is a flowchart illustrating an operation of the gas detection system according to the first embodiment.

An operation of the gas detection system 1000 of the first embodiment will be described with reference to FIG. 3. FIG. 3 is a flowchart illustrating the operation of the gas detection system according to the first embodiment.

Here, the volume of the first space is represented by V1, the gas pressure inside the first space 12 is represented by P1, the volume of the second space is represented by V2, the gas pressure inside the second space 22 is represented by P2, and the atmospheric pressure is represented by P0. For the sake of simplicity, the volume of the specimen 1 is ignored in the description. For the sake of simplicity, the volume V2 of the second space will be described as taking two values of the maximum value V2L and the minimum value V2S, but V2 can take an intermediate value between V2L and V2S. The operation of each unit of the gas concentration device 100 is controlled by the control circuit 70, but description in each step is omitted for simplicity.

In Step S0, the gas concentration device 100 is set to an initial state. That is, the first to fourth shutters 51 to 54 are set to the closed state, V2=V2L, and P2=P0.

Steps S1 to S6 are gas concentration operations of the gas concentration device 100.

In Step S1, the specimen 1 taken in from the intake port (not illustrated) is stored in the first space 12 of the first container 10.

Step S2 is a step in which a gas is discharged from the first space 12. First, the first shutter 51 is opened. Next, the gas is discharged from the first space 12 into the atmosphere by the first vacuum pump 61, and thus a pressure inside the first space 12 is reduced. Thereafter, the first shutter 51 is closed. When a sufficient time has elapsed, a detection target, for example, a gas containing an odor component is released from the specimen 1 into the first space 12 where a gas has already been discharged. The gas in the first space 12 contains a high-concentration (volume % basis) odor component, and the gas pressure is lower than the atmospheric pressure (P1<P0).

Step S3 is a step in which a gas is discharged from the second space 22. In Step S3, first, the third shutter 53 is opened. Next, the gas is discharged from the second space 22 into the atmosphere by the second vacuum pump 62 and thus the pressure inside the second space 22 is reduced. Thereafter, the third shutter 53 is closed. At the end of Step S3, the gas pressure P2 inside the second space 22 is smaller than the gas pressure P1 inside the first space (P2<P1). At the end of Step S3, it is desirable that the second space 22 is in a vacuum state or close to a vacuum state (P2=0).

Step S4 is a step in which the gas containing the high-concentration odor component stored in the first space 12 is fed to the second space 22. In Step S4, the second shutter 52 is opened. In this case, due to a pressure difference between the first space 12 and the second space 22, the gas flows from the first space 12 into the second space 22 until P1=P2. When the volume V2=V2L of the second space 22 is set to be larger than the volume V1 of the first space 12 in Step S4, most of the gas stored in the first space 12 flows into the second space 22, which is more desirable. At the end of Step S4, P2<P0.

Step S5 is a step in which the gas stored in the second space 22 is compressed. In Step S5, first, the second shutter 52 is closed. Thereafter, the pressure control device 30 compresses the second space until the pressure inside the second space slightly exceeds the pressure outside the second space (P2>P0). In this case, the volume V2 of the second space 22 is reduced from V2L to V2S. At the end of Step S5, the gas stored in the second space 22 becomes a concentrated gas containing a high-concentration odor component.

Step S6 is a step in which the concentrated gas stored in the second space 22 is fed to the chemical sensor 200. In Step S6, the fourth shutter 54 enters the first open state. In this case, the concentrated gas having substantially the atmospheric pressure P0 flows into the chemical sensor 200 due to a difference between the gas pressure in the second space 22 and the pressure (atmospheric pressure P0) of the detection section of the chemical sensor 200.

In Step S7, the chemical sensor 200 detects a substance contained in the fed concentrated gas, and outputs an electric signal of a detection result to the determination circuit 300.

In Step S8, the determination circuit 300 analyzes the output signal of the chemical sensor 200, and determines whether a specific substance contained in the gas inspected by the chemical sensor 200 is a specified amount or more. The determination circuit 300 outputs a determination result to the I/F 500. A user can output the determination result to an arbitrary device connected via the I/F 500 and know whether or not a specific odor component is contained in the specimen 1.

In Step S9, the fourth shutter 54 enters the second open state, and the nitrogen gas is fed from the inert gas supply unit 400 to the detection section of the chemical sensor 200.

In the case of continuously inspecting different types of specimens, Steps S1 and S2 may be performed in parallel with Steps S5 and subsequent steps.

Through Steps S0 to S9 described above, the gas detection system 1000 inspects a concentrated gas containing a high-concentration odor component.

An effect of the gas detection system 1000 of the first embodiment will be described.

Some odor components, that is, substances diffusing into the gas phase exist only in a very small amount and a low concentration in the gas phase at normal temperature and normal pressure. In order for a general chemical sensor to achieve accurate and sensitive detection, it is desirable that the object of the detection target is large in amount and high in concentration.

For example, when a gas in the vicinity of a specimen is collected and compressed, a high-concentration odor component-containing gas can be produced on the basis of a substance amount per unit volume (mol/L), but the gas pressure that can be accurately inspected is determined for each type of the chemical sensor 200, and thus, the chemical sensor cannot be used. For example, in the sensitive membrane of the graphene FET, since the conductivity changes by detecting the pressure, noise is generated in the output signal by blowing gas pressurized to a predetermined level or more to the detection section.

In addition, for example, the odor component can be concentrated using adsorption and desorption or condensation of the odor component, but it takes time to concentrate the odor component, and the adsorption property and boiling point vary depending on the type of the odor component, and thus, the entire odor component discharged from the specimen cannot be concentrated.

In the gas detection system 1000, the specimen 1 is stored in the first space 12 having the low pressure state, and thus, the first space 12 is filled with the odor component, and a gas containing a high-concentration odor component can be produced on the basis of a volume ratio (%). The gas inside the first space 12 is transferred to the second space 22 and compressed to near the atmospheric pressure P0, and thus, the odor component is further concentrated to a high concentration on the basis of the amount of substance per unit volume (mol/L).

In the gas concentrated by the gas concentration device 100, the odor component released from the specimen 1 is contained at a high concentration on the basis of a volume ratio (%). That is, since there are few components derived from objects other than the specimen 1 contained in the concentrated gas, the chemical sensor 200 hardly detects noise, and thus, can detect the odor component with high accuracy.

In the gas concentrated by the gas concentrator 100, the odor component discharged from the detection target is contained at a high concentration on the basis of a substance amount per unit volume (mol/L). That is, the amount of the odor component used for one cycle of inspection increases, and the odor component can be detected with high sensitivity.

The gas concentrated by the gas concentrator 100 is fed to the chemical sensor 200 in a state close to atmospheric pressure. Sensing can be performed under stable conditions regardless of the type of the chemical sensor 200, and the odor component can be detected with high accuracy.

The gas concentrator 100 can concentrate the entire odor component diffused from the specimen 1 to the first space 12. In the gas detection system 1000, the odor component can be concentrated in a short time regardless of the type and physical properties of the odor component contained in the specimen 1, and thus, the odor component can be detected with high reliability.

As described above, according to the first embodiment, it is possible to provide the gas detection system 1000 that realizes highly sensitive and highly accurate detection by concentrating odor components derived from the specimen and inspecting the gas.

Modification of First Embodiment

A modification of the first embodiment is different from the first embodiment in that the first vacuum pump 61 and the second vacuum pump 62 are not used to reduce pressures inside the first space 12 and the second space 22 of a gas detection system 1001. Configurations of the gas concentration device 101 and the gas detection system 1001 according to the modification of the first embodiment are the same as those of the gas concentration device 100 and the gas detection system 1000 illustrated in FIG. 1, but the first vacuum pump 61 and the second vacuum pump 62 are in a stopped state. In the modification of the first embodiment, it is considered that an end portion of the first airtight path 41 connected to the first vacuum pump 61 and an end portion of the second airtight path 43 connected to the second vacuum pump 62 are released to the atmosphere (pressure P0).

Hereinafter, an operation of the gas detection system 1001 will be described.

In the modification of the first embodiment, the pressure of the first space 12 and the pressure of the second space 22 are reduced by the pressure control device 30. The operation of the gas detection system 1001 can be realized by replacing Steps S0 to S3 described in the first embodiment with Steps S20 to S23.

In Step S20, the gas concentration device 100 is set to the initial state. That is, the first to fourth shutters 51 to 54 are set to the closed state, and the gas concentration device is set as V2=V2S, and P2=P0.

In Step S21, the specimen 1 is stored in the first space 12.

Step S22 is a step in which the gas is discharged from the first space 12. In Step S22, first, the second shutter 52 is opened. Next, the volume V2 of the second space 22 is increased from V2S to V2L by the pressure control device 30. Subsequently, the second shutter 52 is closed, and the third shutter 53 is opened. Thereafter, the volume V2 of the second space 22 is reduced from V2L to V2S. Finally, the third shutter 53 is closed. By repeating the increase and decrease of the volume V2 an arbitrary number of times, the gas inside the first space 12 is discharged into the atmosphere.

In Step S23, when the second shutter 52, the third shutter 53, and the fourth shutter are closed, the volume V2 of the second space 22 increases from V2S to V2L. Since the volume V2 increases while airtightness of the second space 22 is secured, the gas pressure inside the second space 22 decreases.

In the modification of the first embodiment, since the pressure control device 30 is used to reduce a pressure, it is possible to operate even in a state where one or both of the first vacuum pump 61 and the second vacuum pump 62 have failed. As described above, according to the modification of the first embodiment, the concentration operation can be realized with a simpler configuration than the first embodiment, and the gas concentration device 101 and the gas detection system 1001 having redundancy against failure can be provided.

Second Embodiment

A gas detection system 1002 and a gas concentration device 102 of a second embodiment are different from those of the first embodiment in that a septal membrane type (balloon type) compression mechanism is used as the pressure control device 31.

Figure 4:
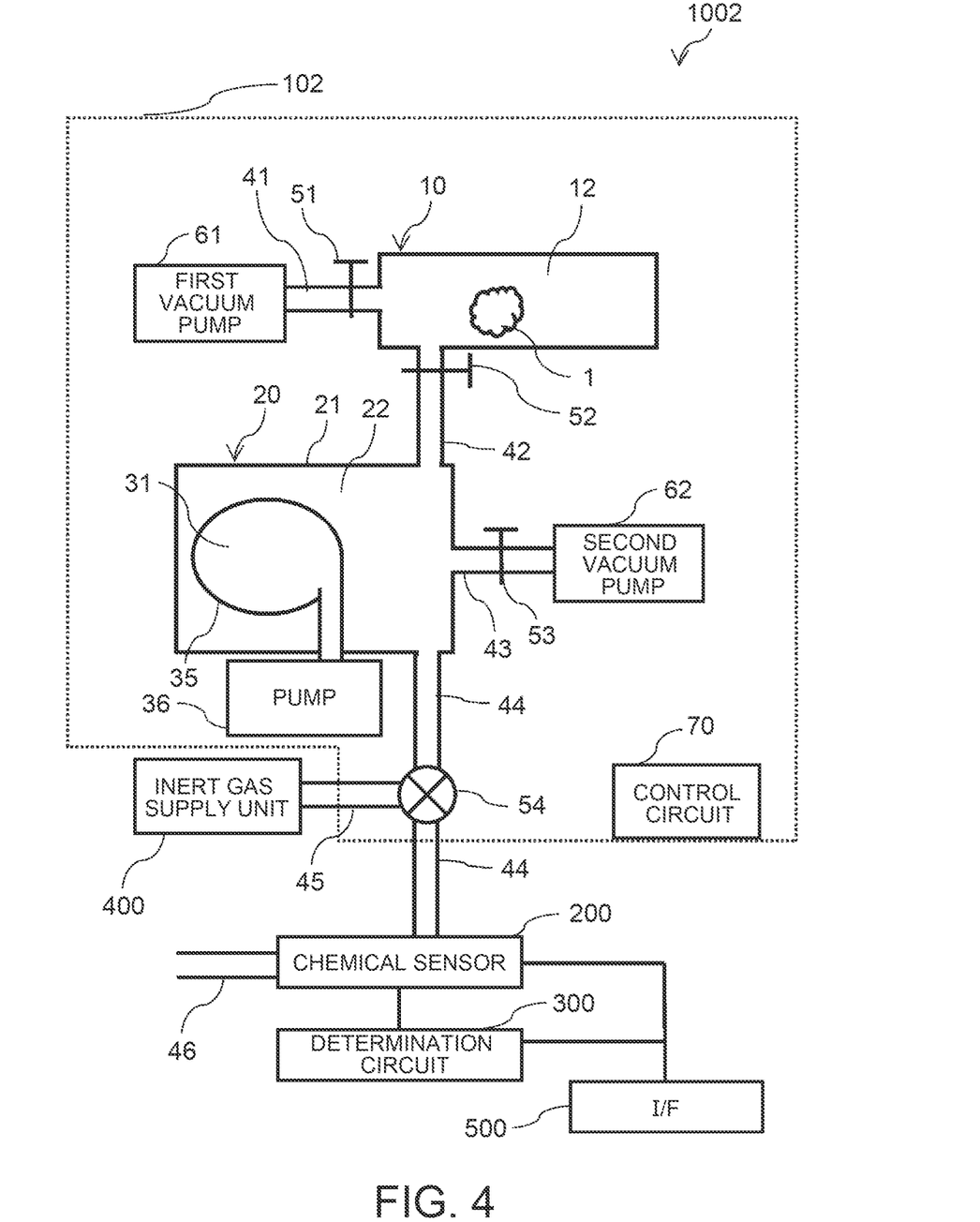
FIG. 4 is a schematic diagram illustrating a configuration of a gas detection system according to a second embodiment.

The gas detection system 1002 according to the second embodiment will be described with reference to FIG. 4. FIG. 4 is a schematic diagram illustrating a configuration of a gas detection system according to a second embodiment.

The pressure control device 31 of the second embodiment includes a septum 35 (partition wall membrane) and a pump 36. The septum 35 is made of a film material through which a gas does not permeate, and has a bag-like shape with a vent. The septum 35 is, for example, a sealed bag made of resin. The septum 35 is provided inside the second space 22 that is kept airtight state. The vent of the septum 35 is connected to the pump 36 outside the second container 20 through the second partition wall 21. The pump 36 expands or contracts the septum 35 and the volume of the gas inside the septum 35 by taking in and out a fluid, for example, air from the outside of the second space 22 into the septum 35. The pressure control device 31 changes the volume V2 of the second space 22 by changing the volume of the septum 35 occupying the entire volume of the second space 22.

The pressure control device 31 of the second embodiment does not include a compression mechanism driven by a structure close in contact with the partition wall for maintaining airtightness of the second space 22. Therefore, a gas does not leak from a gap between the partition wall and the structure, for example, a gap between a piston and a cylinder in the piston-type compression mechanism. That is, concentration efficiency of the gas concentration device 102 is improved, and the gas detection system 1002 can realize high detection sensitivity.

In addition, since the pressure control device 31 of the second embodiment does not have a portion that is mechanically driven and rubbed, a lubricant volatilized by friction and a component derived from a worn part are hardly mixed with the concentrated gas. Therefore, detection accuracy and reliability of the chemical sensor 200 are improved.

According to the second embodiment, it is possible to provide the gas concentration device 102 having higher concentration efficiency than that of the first embodiment and the gas detection system 1002 having higher sensitivity and higher accuracy than that of the first embodiment.

Third Embodiment

A gas detection system 1003 of a third embodiment is different from the concentration device of the first embodiment in that an expansion/contraction chamber type (accordion type) compression mechanism is used as a pressure control device 32.

Figure 5:
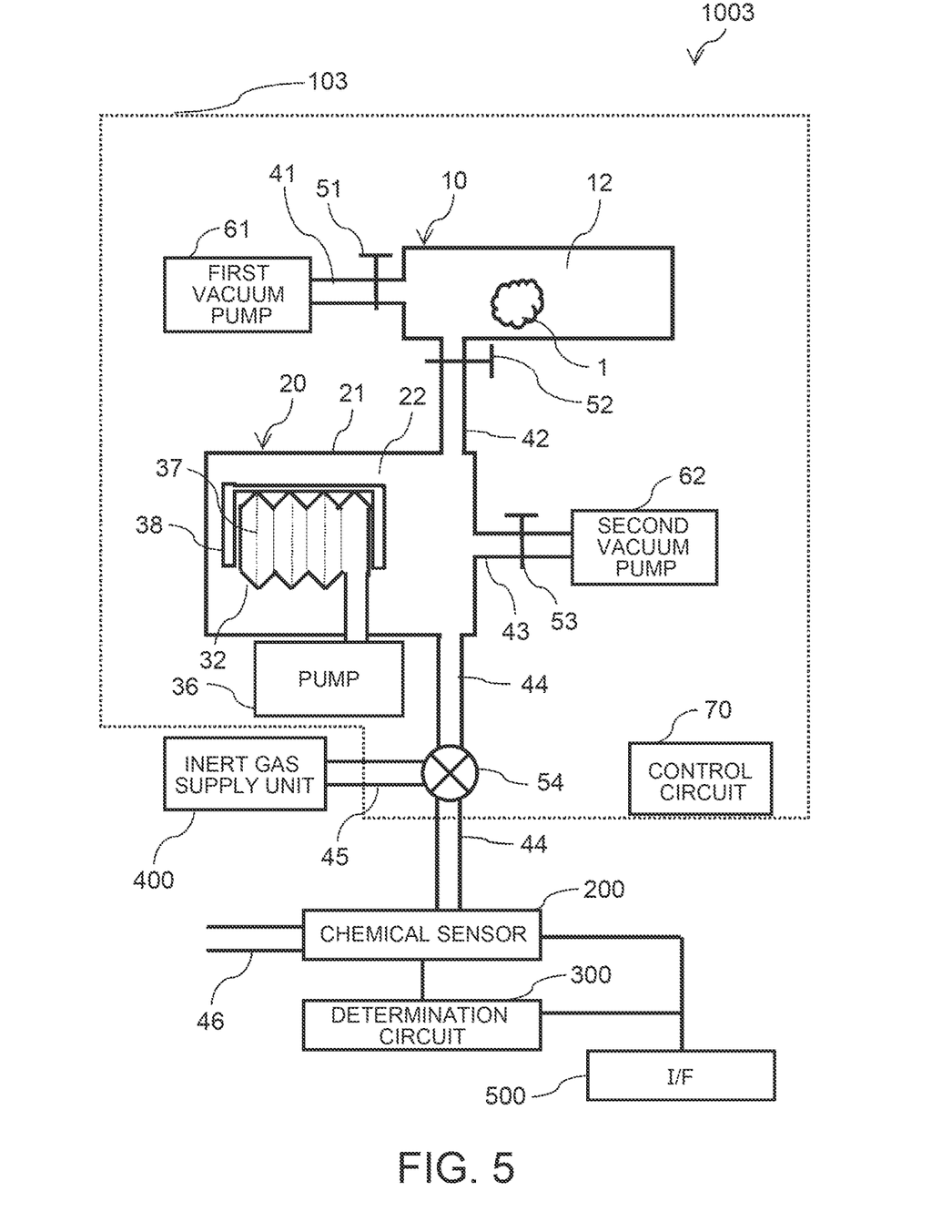
FIG. 5 is a schematic diagram illustrating a configuration of a gas detection system according to a third embodiment.

The gas detection system 1003 according to the third embodiment will be described with reference to FIG. 5. FIG. 5 is a schematic diagram illustrating a configuration of the gas detection system 1003 according to the third embodiment.

The pressure control device 32 of the third embodiment includes a partition wall 37 and a drive device 38. The partition wall 37 has an airtight structure therein, the partition wall 37 is deformed by expansion and contraction, and thus, a volume of an airtight space inside the partition wall 37 is changed. The partition wall 37 has, for example, a foldable bellows structure, and has a bellows-like shape with a vent connected to the airtight space of the partition wall 37. The partition wall 37 is provided inside the second space 22 of the second container 20 in an airtight state. The vent penetrates the second partition wall 21 and is connected to the pump 36 outside the second space 22 so as to maintain airtightness of the second space 22. The partition wall 37 prevents gas from flowing between an airtight space inside the partition wall 37 and the second space 22. The drive device 38 changes the volumes of the partition wall 37 and the internal space by lengthening and shortening a distance between both ends of the bellows structure of the partition wall 37. The drive device 38 may be provided inside the partition wall 37. The volume of the partition wall 37 may be changed by taking a fluid in and out of the internal space of the partition wall 37 using the pump 36 described in the second embodiment instead of the drive device 38.

The pressure control device 32 changes the volume V2 of the second space 22 by changing the volumes of the partition wall 37 and the internal airtight space.

The pressure control device 32 of the third embodiment prevents gas from leaking from the gap of the partition wall. That is, the gas detection system 1003 can realize high concentration efficiency and high sensitivity. Since the pressure control device 32 of the third embodiment does not have a portion that is mechanically driven and rubbed, a lubricant volatilized by friction and a component derived from a worn part are hardly contained in the concentrated gas. Therefore, detection accuracy and reliability of the chemical sensor 200 are improved.

Unlike the pressure control device 32 of the second embodiment, the pressure control device 31 of the third embodiment does not necessarily require the pump 36. The pressure control device 32 can be downsized as compared with the pressure control device 31 by omitting the pump 36. The volume of the partition wall 37 of the pressure control device 32 is controlled by the drive and displacement amount of the drive device 38. That is, the volume of the partition wall 37 of the pressure control device 32 is hardly affected by the internal pressure P2 of the second space 22 that is greatly changed by the operation of each step. The pressure control device 32 can control the volume V2 of the second space 22 with higher accuracy than the pressure control device 31.

According to the third embodiment, it is possible to provide the concentration device 103 having higher concentration efficiency than that of the first embodiment and the gas detection system 1003 having higher sensitivity and higher accuracy than that of the first embodiment.

Fourth Embodiment

A gas concentration device 104 and a gas detection system 1004 of a fourth embodiment are different from those of the first embodiment in that a pressure control device 33 is also provided in a first container 10.

Figure 6:
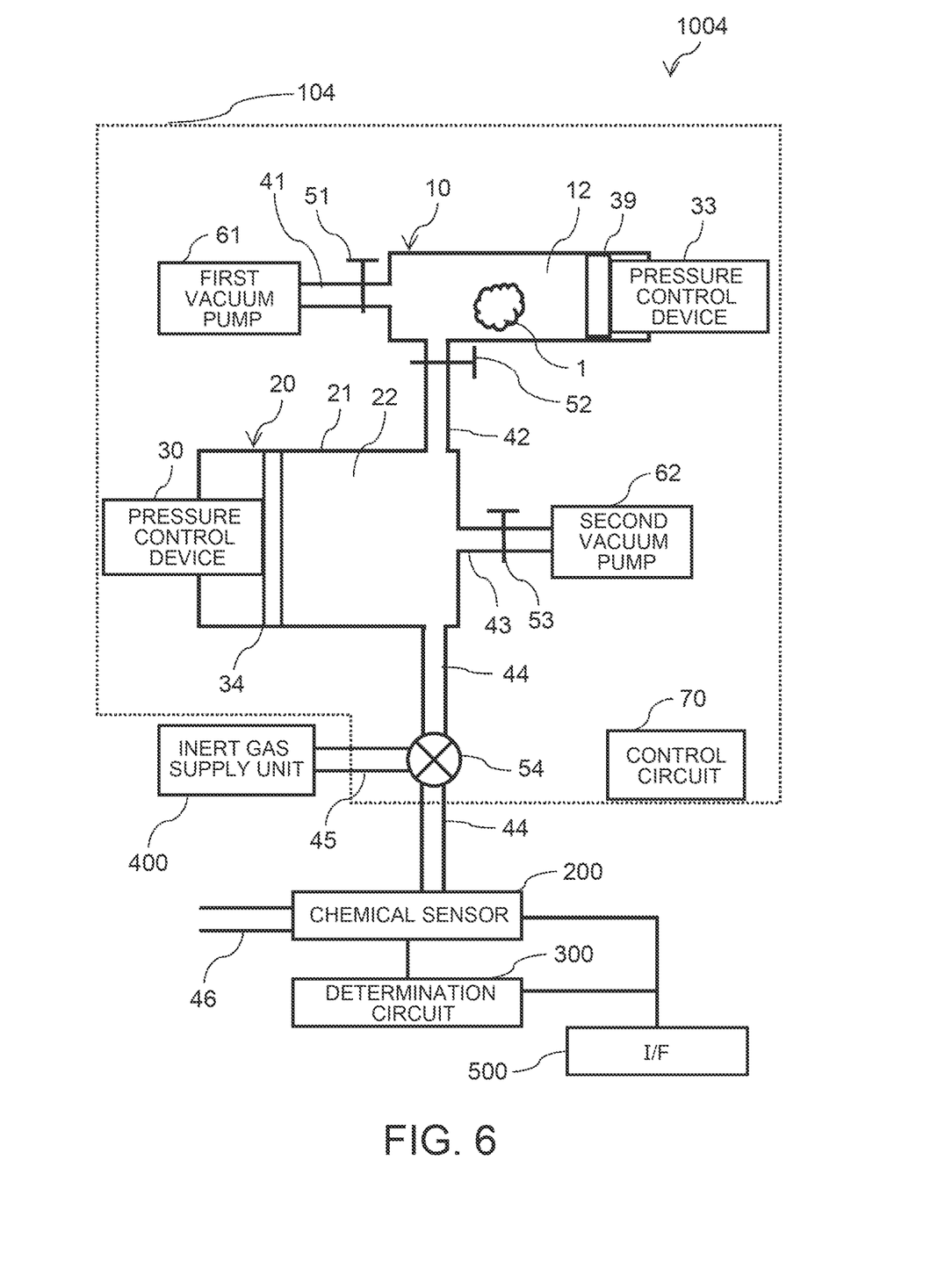
FIG. 6 is a schematic diagram illustrating a configuration of a gas detection system according to a fourth embodiment.

The gas detection system 1004 according to the fourth embodiment will be described with reference to FIG. 6. FIG. 6 is a schematic diagram illustrating a configuration of the gas detection system 1004 according to the fourth embodiment.

The pressure control device 33 is a device that changes the volume of the first space 12, and can be realized by a structure similar to that of the pressure control device 30. In Step S4 of the first embodiment, the pressure control device 33 contracts the volume of the first space 12. In Step S4, when the second shutter 52 is opened, an amount of gas corresponding to a ratio of V2 and (V1+V2) flows from the inside of the first space 12 into the second space until it becomes P1=P2. As the volume V1 of the first space 12 decreases, the value of V2/(V1+V2) increases. The amount of gas fed from the inside of the first space 12 to the second space 22 increases, and the amount of gas that can be compressed in the second space 22 increases. Therefore, the amount of odor components to be concentrated increases, and the concentration efficiency of the gas concentration device 104 is improved.

As described above, according to the fourth embodiment, it is possible to provide the gas concentration device 104 having a concentration efficiency higher than that of the first embodiment and the gas detection system 1004 having high sensitivity.

Fifth Embodiment

A gas concentration device 105 and a gas detection system 1005 of a fifth embodiment are different from those of the first embodiment in including a heater 80.

Figure 7:
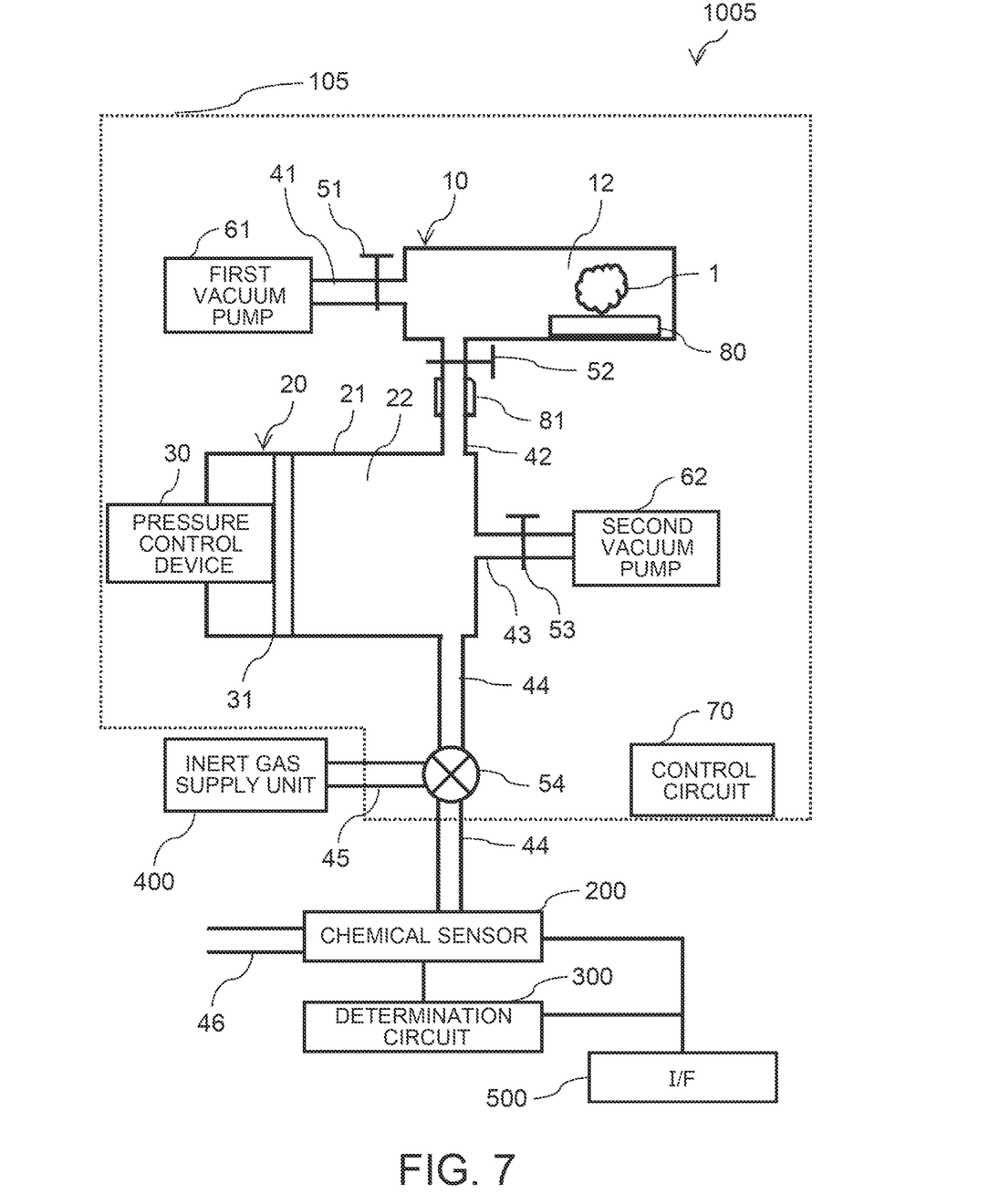
FIG. 7 is a schematic diagram illustrating a configuration of a gas detection system according to a fifth embodiment.

The gas detection system 1005 according to the fifth embodiment will be described with reference to FIG. 7. FIG. 7 is a schematic diagram illustrating a configuration of the gas detection system 1005 according to the fifth embodiment.

A heater 80 is provided in the first container 10 of the fifth embodiment. The heater 80 directly or indirectly heats the specimen 1 to promote volatilization of odor components and increase the amount of odor components to be concentrated. A temperature of the heated specimen 1 is higher than an environmental temperature at which the gas detection system 1005 is placed.

A cooling device 81 may be further provided inside the first container 10 or in the airtight path 42 of the fifth embodiment. The cooling device 81 condenses and separates moisture evaporated from the specimen 1 by cooling the moisture by the heater 80. By the separation of the moisture, a ratio of the odor component contained in the gas flowing into the second space 22 increases, and thus, concentration efficiency of the gas concentration device 105 is improved. In particular, in a case where a solidifying point of the odor component is lower than a solidifying point of water, it is possible to realize a configuration in which the odor component is not removed while moisture is removed by setting the temperature of the cooling device 81 to an intermediate temperature between both solidifying points.

As described above, according to the fifth embodiment, it is possible to provide the gas concentration device 105 having a concentration efficiency higher than that of the first embodiment and the gas detection system 1005 having high sensitivity.

Sixth Embodiment

A gas concentration device 106 and a gas detection system 1006 of a sixth embodiment are different from those of the first embodiment in not including a first container 10.

Figure 8:
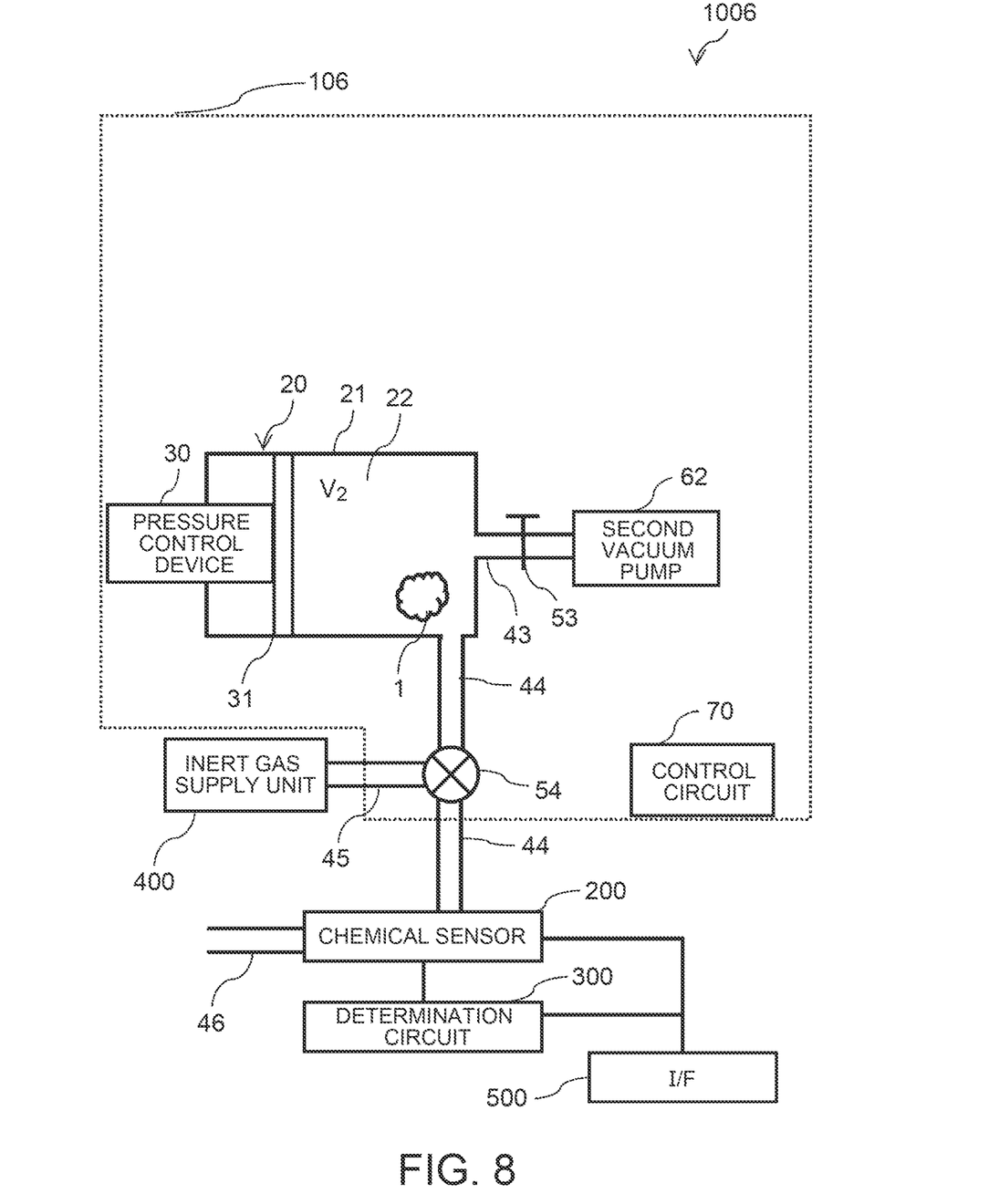
FIG. 8 is a schematic diagram illustrating a configuration of a gas detection system according to a sixth embodiment.

The gas detection system 1006 according to the sixth embodiment will be described with reference to FIG. 8. FIG. 8 is a schematic diagram illustrating a configuration of the gas detection system 1006 according to the sixth embodiment.

In the gas concentration device 106 of the sixth embodiment, the specimen 1 is stored in the second space 22.

An operation of the gas detection system 1006 will be described. The operation of the gas detection system 1006 can be realized by replacing Steps S1 to S4 described in the first embodiment with Steps S11 and S12.

In Step S11, the specimen 1 is stored in the second space 22.

Step S12 is a step in which a gas is discharged from the second space 22. In Step S12, first, the third shutter 53 is opened. Next, the gas is discharged from the second space 22 to the atmosphere by the second vacuum pump 62, and then the third shutter 53 is closed. When a sufficient time has elapsed, the odor component is released from the specimen 1 into the second space 22 where the gas has already been discharged.

In the gas detection system 1006, Step S12 of diffusing the odor component under a low pressure environment and Step S5 of compressing the odor component are realized in the same second container 20. Therefore, a plurality of steps cannot be performed in parallel, and it takes time to perform the operation of the continuous cycle, but the concentration operation can be realized with a simple configuration.

As described above, according to the sixth embodiment, it is possible to provide the gas concentration device 106 and the gas detection system 1006 capable of realizing the concentration operation with a simpler configuration than that of the first embodiment.

The first to sixth embodiments can be implemented by appropriate combination. For example, the septal membrane type compression mechanism or the expansion/contraction chamber type compression mechanism may be adopted as the pressure control device 33 provided in the first container 10. Other than this, any combination of first to sixth embodiments is allowed. According to the first to sixth embodiments described above, it is possible to provide the gas detection system that realizes highly sensitive and highly accurate detection by concentrating odor components derived from the specimen and inspecting gas.

Although some embodiments of the present invention have been described, these embodiments have been presented as examples, and are not intended to limit the scope of the invention. The embodiments can be implemented in various other forms, and various omissions, substitutions, and changes can be made without departing from a gist of the invention. These embodiments and modifications thereof are included in the scope and gist of the description and are included in the invention described in the claims and an equivalent scope thereof.

What is claimed is:
1. A gas concentration device comprising:
a first container that includes a first space surrounded by a first partition wall and stores a specimen, the first container configured to store a gas containing an odor component released from the specimen into the first space where a pressure is reduced;

a second container that is connected to the first container by a first path and has a second space surrounded by a second partition wall and configured to store a gas containing the odor component flowing in from the first space;
a pressure control device configured to reduce a volume of the second space and configured to concentrate the gas containing the odor component;
a second path through which a gas containing the odor component inside the second space is discharged; and
a first decompression device that is connected to the first space by a third path and reduces a pressure inside the first space.

2. The gas concentration device according to claim 1, further comprising a second decompression device that is connected to the second space by a fourth path and reduces a pressure inside the second space.

3. The gas concentration device according to claim 1, wherein
the second partition wall has a tubular shape, and
the pressure control device further includes a third partition wall that is in close contact with an inner wall of the second partition wall and moves in a direction in which the tubular shape extends, and a first drive device that moves the third partition wall.

4. The gas concentration device according to claim 1, wherein the pressure control device further includes a fourth partition wall that is provided inside the second space and has a bag-like shape with an open vent, and a pump that is airtightly connected to the vent and takes in and out a fluid between outside of the second space and inside of the fourth partition wall.

5. The gas concentration device according to claim 1, wherein the pressure control device further includes a fifth partition wall that is provided inside the second space, which has a space inside with respect to the second space, and is expandable and contractible, and a second drive device that expands and contracts the fifth partition wall.

6. The gas concentration device according to claim 1, further comprising a second pressure control device that increases or decreases a volume of the first space.

7. The gas concentration device according to claim 1, wherein the first container further includes a heater that heats the specimen.

8. The gas concentration device according to claim 1, further comprising a cooler that cools the first path.

9. The gas concentration device according to claim 1, further comprising:
a first shutter that switches the first path between an open state in which a gas can flow and a closed state in which a gas cannot flow; and
a second shutter that switches the second path between an open state in which a gas can flow and a closed state in which a gas cannot flow.

10. The gas concentration device according to claim 1, wherein the pressure control device increases the volume of the second space to reduce a pressure inside the first space.

11. The gas concentration device according to claim 1, wherein the pressure control device increases the volume of the second space to reduce a pressure inside the second space.

12. The gas concentration device according to claim 1, wherein the pressure control device reduces the volume of the second space until a pressure inside the second space exceeds a pressure outside the second space.

13. The gas concentration device according to claim 1, further comprising:
a second decompression device that is connected to the second space by a fourth path and configured to reduce a pressure inside the second space;
a first shutter configured to switch the first path between an open state in which a gas can flow and a closed state in which a gas cannot flow;
a second shutter configured to switch the second path between an open state in which a gas can flow and a closed state in which a gas cannot flow; and
a control circuit configured to control the first shutter, the second shutter, the first decompression device, the second decompression device, and the pressure control device, wherein the control circuit is configured to control
an operation in which the first decompression device is configured to reduce the pressure inside the first space in a state where the first shutter is closed,
an operation in which the second decompression device is configured to reduce the pressure inside the second space in a state where the first shutter and the second shutter are closed,
an operation in which the first shutter is configured to switch to an open state,
an operation in which the first shutter is configured to switch to a closed state and the pressure control device reduces a volume of the second space, and
an operation in which the second shutter is configured to switch to an open state.

14. The gas concentration device according to claim 1, further comprising:
a control circuit that controls an operation of the gas concentration device, wherein the control circuit controls
an operation in which a pressure inside the first space is reduced,
an operation in which a pressure inside the second space is reduced,
an operation in which a gas is fed from the first space to the second space,
an operation in which the pressure control device compresses the gas inside the second space, and
an operation in which the gas is discharged from the second space.

15. A gas detection system comprising:
the gas concentration device according to claim 1; and
a chemical sensor that detects a detection target from a gas containing a substance of the detection target discharged from the second path.

16. The gas detection system according to claim 15, further comprising a determination circuit that is connected to an output of the chemical sensor, determines whether the chemical sensor has detected a first gas, and outputs a determination result.

17. A gas concentration method comprising:
storing a gas and a specimen in a first container;
reducing a pressure inside the first container and releasing a gas containing an odor component from the specimen;
feeding the gas stored in the first container to an inside of a second container connected to the first container;
compressing the gas stored inside the second container; and
discharging the compressed gas from the second container.

18. A gas detection method comprising:
storing a gas and a specimen in a first container;

reducing a pressure inside the first container and releasing a gas containing an odor component from the specimen;

feeding the gas stored in the first container to an inside of a second container connected to the first container;

compressing the gas stored inside the second container;

discharging the compressed gas from the second container; and discharging the gas discharged from the second container onto a chemical sensor.

19. The gas concentration device according to claim 1, wherein the first decompression device is a first vacuum pump.

20. The gas concentration device according to claim 2, wherein the second decompression device is a second vacuum pump.

21. The gas concentration device according to claim 13, wherein the first decompression device is a first vacuum pump and the second decompression device is a second vacuum pump.

22. A gas concentration device comprising:

a first container that includes a first space surrounded by a first partition wall and stores a specimen, and a pressure inside the first space is reduced;

a second container that is connected to the first container by a first path and has a second space surrounded by a second partition wall and configured to store a gas flowing in from the first space;

a pressure control device configured to reduce a volume of the second space; and a second path through which a gas inside the second space is discharged, wherein the pressure control device further includes a fourth partition wall that is provided inside the second space and has a bag-like shape with an open vent, and a pump that is connected to the vent and takes in and out a fluid between outside of the second space and inside of the fourth partition wall.

* * * * *